United States Patent [19]
Pruter

[11] Patent Number: 5,910,113
[45] Date of Patent: Jun. 8, 1999

[54] SHEATH FOR ULTRASOUND PROBE

[76] Inventor: Rick L. Pruter, 611 Southgate Ave., Iowa City, Iowa 52240-2166

[21] Appl. No.: 09/047,062

[22] Filed: Mar. 24, 1998

[51] Int. Cl.⁶ ........................................................ A61B 8/00
[52] U.S. Cl. ............................................ 600/437; 128/918
[58] Field of Search ................................... 600/437, 459; 128/844, 918

[56] References Cited

U.S. PATENT DOCUMENTS

| | | | |
|---|---|---|---|
| 4,593,699 | 6/1986 | Poney et al. | 600/437 |
| 5,259,383 | 11/1993 | Holstein et al. | 600/437 |
| 5,351,698 | 10/1994 | Wheeler, deceased et al. | 128/844 |
| 5,355,886 | 10/1994 | Dominque et al. | 600/437 |
| 5,651,374 | 7/1997 | Wester | 128/844 |
| 5,666,972 | 9/1997 | Gifford | 128/844 X |

OTHER PUBLICATIONS

Rui, M "Device for placing a Protective Sheath Over an Organ of the Body" Intnl Appln Published Under the PCT, WO92/06657, Apr. 30, 1992.

Andrews, G. et al "Gordan Packaging", Intnl Appln Published Under the PCT, WO95/02379, Jan. 26, 1995.

*Primary Examiner*—Francis J. Jaworski
*Attorney, Agent, or Firm*—Alan L. Harms

[57] ABSTRACT

An improved sheath for use to cover an ultrasound transducer probe. An elongate polymeric tube is telescopingly collapsed upon itself toward its open end. An open-ended polygonal body is mounted within the tube adjacent its open end. The body is flattened until ready for use, whereupon it may be formed into a three-dimensional body and used to form a passage for the probe into the tube. Conductive gel is deposited into the tube at its lower end and a transducer probe passed through the body in the tube. The user may then grasp the open end of the sheath in one hand and the probe within the tube in the other hand and draw the tube into its fully extended form for use.

10 Claims, 4 Drawing Sheets

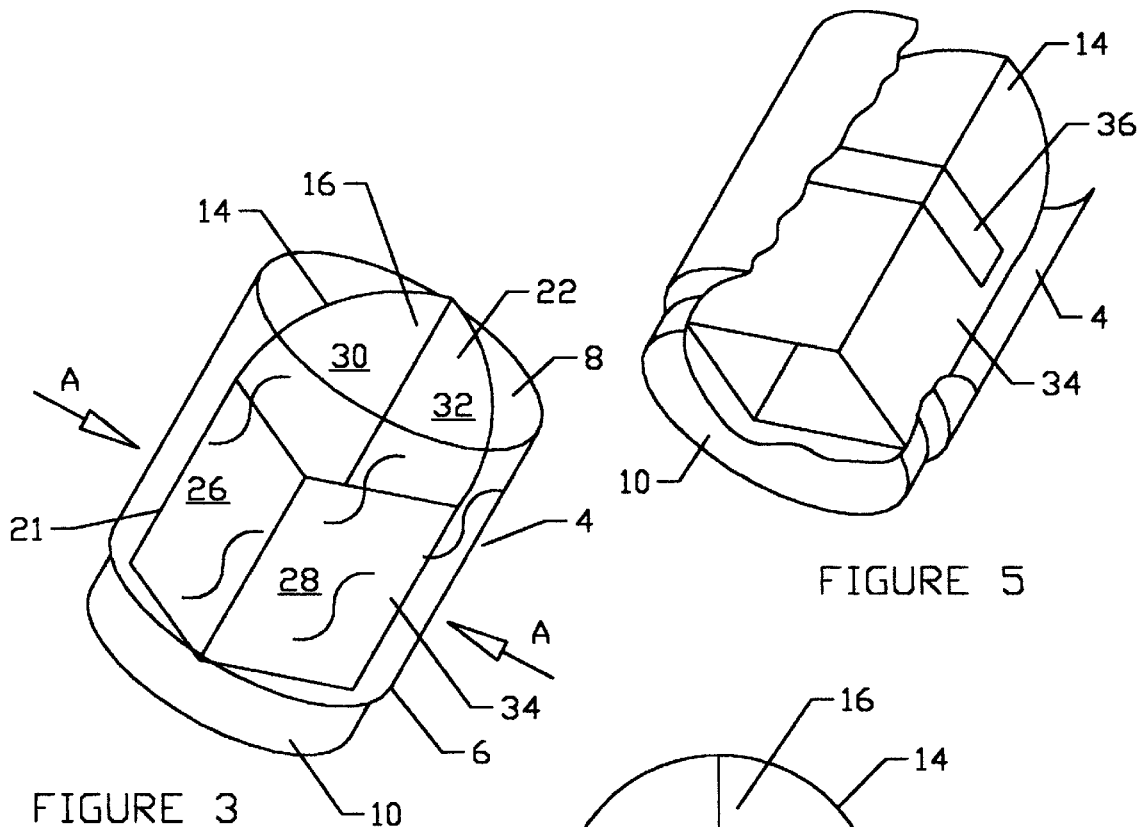
FIGURE 3
FIGURE 5
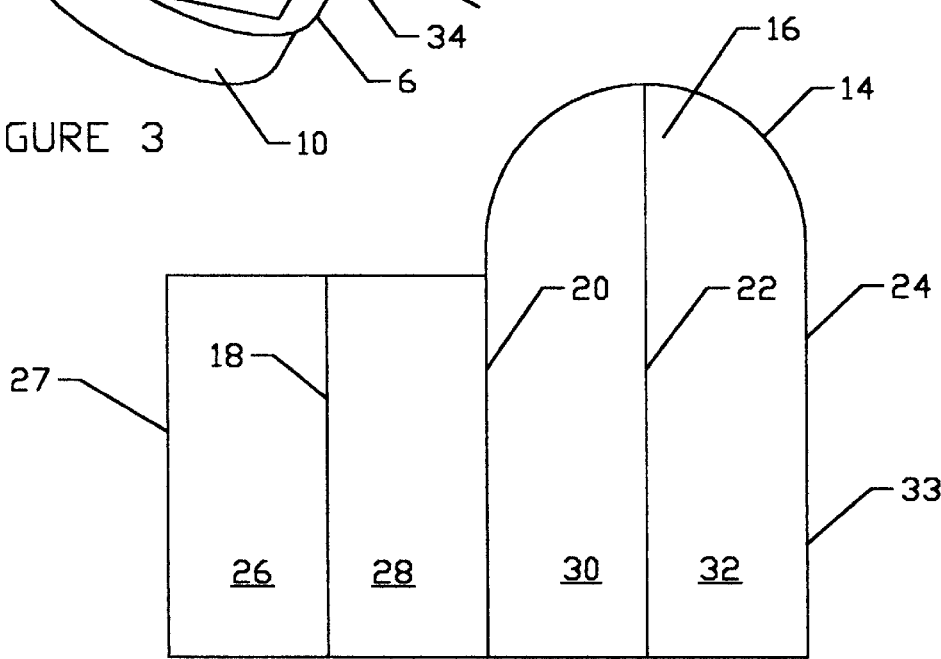
FIGURE 4

SHEATH FOR ULTRASOUND PROBE

BACKGROUND OF THE INVENTION

In the use of ultrasound imaging in the performance of medical procedures, it is frequently desired to encapsulate the ultrasound transducer probe in a disposable sterile sheath. The use of the sterile sheath protects the patient when endocavity ultrasound imaging is to be performed or when the patient's skin is to be pierced for performance of amniocentesis or biopsy collection. The use of the sheath also protects a patient or health care professional from cross contamination from the probe.

In the usual sheath, an elongate bag of polymeric material such as latex, polyethylene, or polyurethane is opened and a quantity of conductive gel is placed in the sheath to aid in transduction of ultrasound energy to the probe. Because the bag may be eighteen or more inches long and fairly narrow, it is difficult to place the gel at the bottom of the bag where it is needed without having gel distributed along the length of the interior of the bag thereby causing the transducer probe body and its attached signal cable to be coated unnecessarily with gel when the transducer is placed in the bag. This necessitates the use of wasted conductive gel and the need to remove gel from the body of the probe and its cabling when the procedure is completed. Therefore, there is a need to provide a sheath which facilitates the placement of conductive gel at the bottom of the sheath where it is useful in cooperation with the transducer probe operative surfaces.

SUMMARY OF THE INVENTION

The present invention provides an improved sheath for receiving an ultrasound transducer probe used in ultrasound imaging in medical practice, especially for endocavity imaging and when a sterile operative field must be maintained.

An elongate flexible polymeric bag, typically of latex, polyethylene, or polyurethane, is provided with an open upper end in which is placed a collapsed polygon having open ends. In the preferred embodiment, the polygon is a rectangular or square tube which is flattened into abutting sheets of relatively stiff material such as paper board. The collapsed polygon is placed inside the bag near the upper open end and is fixed to the bag with adhesive or other suitable means. The bag is telescopingly collapsed or rolled upon itself at its upper end such that the collapsed bag surrounds the flattened polygon. When the sheath is to be used, the user may grasp the collapsed sheath and squeeze the edges of the flattened polygon to expand it into a polygon and may then place conductive gel in the closed bottom end of the tube followed by insertion of the transducer probe into the bag through the expanded polygon. The user may then grasp the sheathed probe and draw the probe and its cable through the polygon and telescopingly expand the tube as the probe is drawn away from the polygon.

DESCRIPTION OF THE DRAWING FIGURES

FIG. 3 is a front perspective view of the invention showing the polygonal insert in its expanded condition but with the polymeric tube telescoped upon itself around the insert.

FIG. 4 is a front elevation of a scored blank which may be formed into the insert of the preferred embodiment of the invention.

FIG. 5 is a rear perspective of the invention with the bag partially cutaway showing the insert formed into a polygon and disposed in the upper end of the flexible tube of the invention.

DETAILED DESCRIPTION OF THE INVENTION

Figure 1:
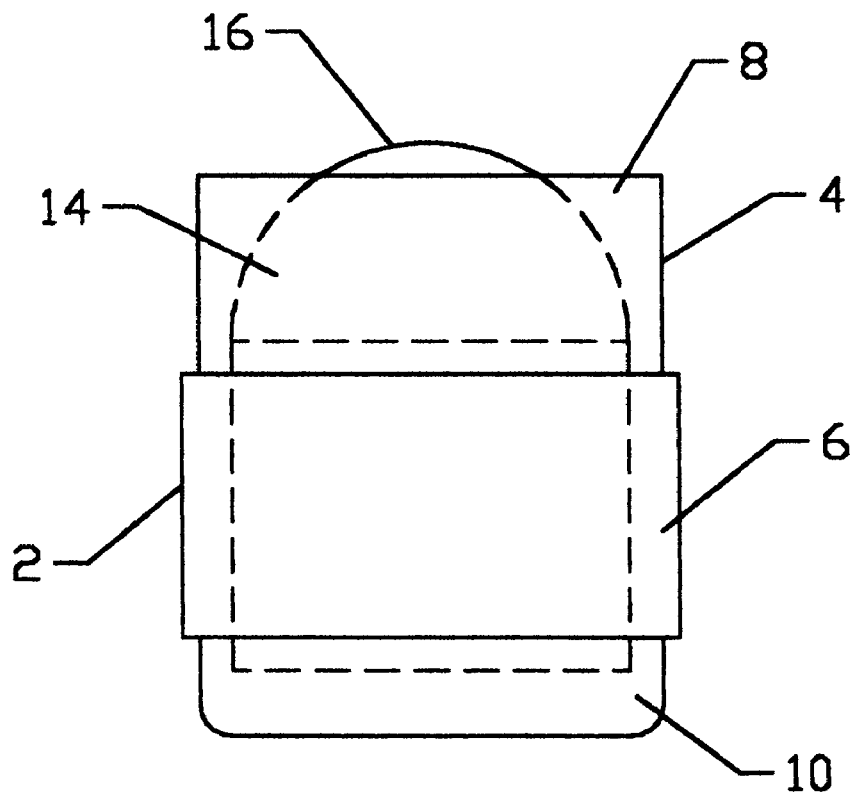
FIG. 1 is a front elevation of the invention in its collapsed state.

Referring to the drawings and particularly to FIG. 1, the invention probe sheath may be viewed in its initial state before expansion thereof in preparation for reviewing an ultrasonic transducer probe. The invention 2 includes an elongate tube 4 of flexible polymeric material, preferably transparent or translucent polyethylene, latex, or polyurethane, having an open upper end 8 and closed lower end 10 disposed on opposing ends of sidewall 6. The elongate tube 4 is telescopingly collapsed upon itself by rolling or folding the sidewall 6 of the elongate tube 4 repeatedly upon itself. In the preferred embodiment, sidewall 6, upper end 8, and lower end 10 are integral parts of elongate tube 4. Because elongate tube 4 is constructed of flexible polymeric material, sidewall 6 can easily be rolled or folded upon itself to effectively shorten the length of elongate tube 4 when it is to be formed in its initial collapsed state. Insert 14 is disposed within open upper end 8 and sidewall 6 of elongate tube 4 and remains flat in the initial state of invention 2. Insert 14 is provided with a curved tab 16 which extends from upper end 8 of elongate tube 4.

Figure 2:
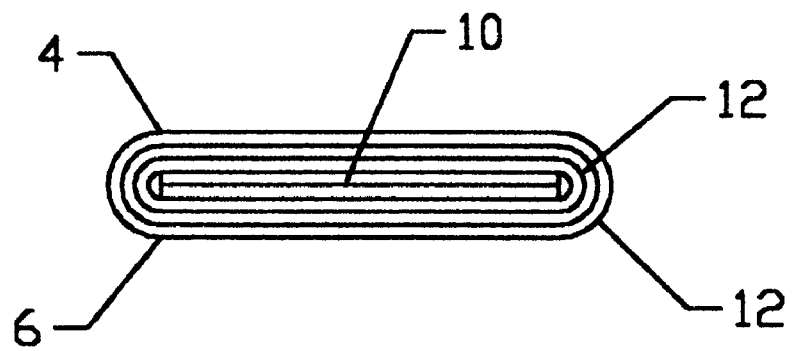
FIG. 2 is a bottom plan view of the sheath invention shown in the collapsed state.

FIG. 2 discloses a bottom end view of invention 2 wherein the multiple folds 12 of sidewall 6 may be visualized with lower end 10 being disposed centrally within folds 12 of sidewall 6.

In the preferred embodiment, insert 14 is easily expandable into a four-sided box in the second partly expanded state of invention 2 due to the imposition during the manufacturing process of score lines 18, 20, and 22 on insert 14 while it remains in a flat blank 24 as shown in FIG. 4. Blank 24 in the preferred embodiment is cut from generally lightweight, thin-walled, inexpensive material such as card stock or rigid plastic sheet. Score lines 18, 20 and 22 are placed on blank 24 by conventional means such that blank 24 can easily be folded about score line 20 such that first panel 26 and second panel 28 will abut fourth panel 32 and third panel 30 respectively, with the result that insert 24 initially is a planar object which may be inserted into elongate tube 4 while elongate tube 4 remains in its collapsed initial state as seen in FIG. 1.

Referring now to FIG. 3, invention 2 can be seen in its second, partly expanded state. It is to be understood that a user exerts pressure on opposing sides of sidewall 6 in the direction of arrows A whereby insert 14 is caused to expand into an open ended polygon 34. The imposition of forces in the direction of arrows A is preferably made between the thumb and forefinger of a user's hand forcing hinge 21 along score line 20 toward first fee edge 27 of blank 24 and second free edge 33 of blank 24 which are juxtaposed when blank 24 is folded about center score line 20, thereby causing first panel 26 to angularly deflect from fourth panel 32 and second panel 28 to angularly deflect from third panel 30 such that panels 26 and 28 hinge about score line 18 and panels 30 and 32 hinge about score line 22 and thereby insert 14 is formed into polygon 34 which, in the preferred embodiment, is a square box having open ends.

FIG. 5 illustrates the rear of invention 2 wherein the preferred structure for affixing insert 14 to elongate tube 4 is disclosed showing double sided adhesive tape 36 affixed to insert 14 and to elongate tube 4. Alternate means to fix insert 14 near upper end 8 and within elongate tube 4 are contemplated including other adhesive means or by stapling. It is found that adhesive means such as double sided tape 36 is preferable to avoid possible inadvertent loss of staples or other mechanical fixation elements while the invention is in use during a medical procedure.

It is to be understood that an important consideration in design of invention 2 is to permit effective deposition of conductive gel within elongate tube 4 before insertion of a transducer probe therein, such conductive gel being useful to establish a sonic transmission medium from the transducer probe to closed lower end 10 of tube 4. The conductive gel may be easily deposited within the elongate tube 4 into lower end 10 by directing the gel downward through polygon 34 into closed lower end 10 while the tube 4 remains telescoped upon itself.

Figure 6:
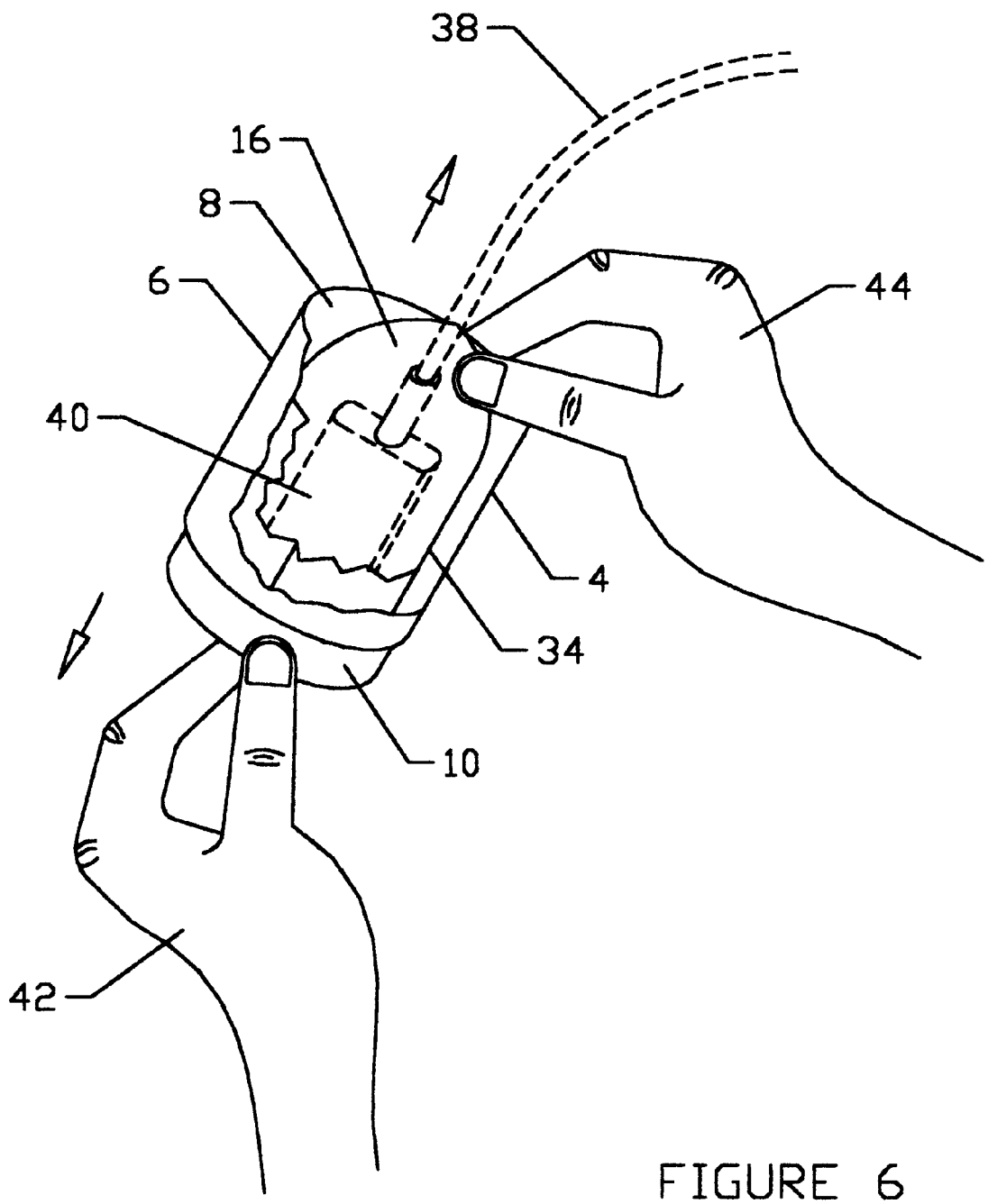
FIG. 6 is a perspective view of the invention shown partly cutaway with a transducer probe shown being placed in the sheath and showing the hands of a user drawing the probe downward and pulling the insert upward.

FIG. 6 discloses the invention 2 in its second partly expanded state after a transducer probe 40 has been introduced into elongate tube 4 through insert 14 after insert 14 has been formed into polygon 34 and after a conductive gel has been placed into closed lower end 10 of elongate tube 4. The user of invention 2 may grasp transducer probe 40 from outside tube 4 with the user's fingers, the left hand 42 being illustrated in FIG. 6, while the fingers of the user's opposite hand, (right hand 44) may grasp tab 16 along with sidewall 6 of elongate tube 4 at the upper end 8 thereof and pull closed end 10 away from open end 8 while drawing transducer probe cable 38 into elongate tube 4.

Figure 7:
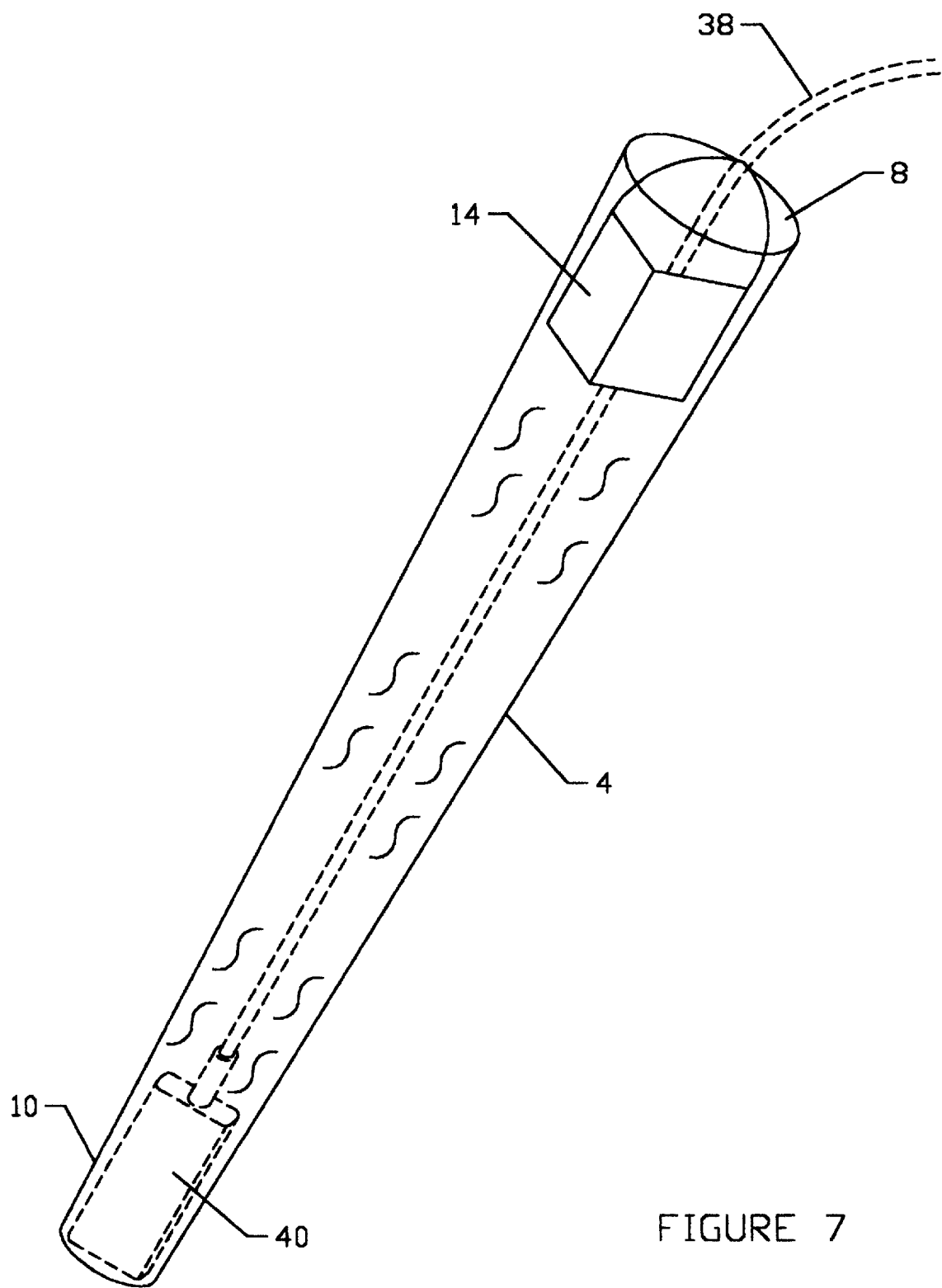
FIG. 7 is a perspective of the invention sheath fully expanded with a transducer probe disposed in the bottom end of the sheath.

FIG. 7 illustrates invention 2 in its third fully expanded state wherein elongate tube 4 has been drawn to its full length with all folds removed, with transducer probe 40 disposed within lower end 10 of elongate tube 4 and with insert 14 affixed near open end 8 of tube 4 from which transducer cable 38 extends. In this state, the sheath is fully deployed and the transducer probe is ready for use.

Having described the invention.

I claim:

1. An elongate sheath for receiving an ultrasound transducer probe comprising a tube of flexible polymeric material having an open end and an opposing closed end;

a polygonal body having open opposing ends;

one of said open ends of said polygonal body disposed at said open end of said tube;

said polygonal body disposed within said tube near the open end thereof;

said polygonal body constructed of relatively stiff material;

said polygonal body collapsible into a substantially planar object;

said polygonal body retained to said tube;

said tube telescopingly collapsed about said polygonal body.

2. The sheath of claim 1 wherein said tube is constructed from the group consisting of polyethylene, latex, and polyurethane.

3. The sheath of claim 1 wherein said polygonal body comprises a formed blank separated into adjacent panels by parallel score liners.

4. The sheath of claim 3 wherein said blank is separated into four panels.

5. The sheath of claim 1 wherein said polygonal body comprises a four-sided box.

6. The sheath of claim 5 wherein said polygonal body is constructed of card stock.

7. The sheath of claim 1 wherein said tube having an elongate sidewall between the ends thereof;

said sidewall telescopingly folded upon itself in a first state of said sheath;

in a second state, said sidewall being extended without folds thereon.

8. The sheath of claim 1 wherein said polygonal body having a first end and a second end;

said first end coaxial with said open end of said tube;

said polygonal body having a tab extending from said open end of said tube.

9. The sheath of claim 1 wherein said polygonal body comprises a blank separated into adjacent panels by parallel score liners;

said blank is separated into four panels;

said polygonal body comprises a four-sided box;

said polygonal body is constructed of card stock;

said tube having an elongate sidewall between the ends thereof;

said sidewall telescopingly folded upon itself in a first state of said sheath;

in a second state, said sidewall being extended without folds thereon.

10. A protective enclosure for receiving an ultrasound transducer probe comprising a tube of flexible polymeric material having an open end;

a sheet of relatively stiff material disposed within said tube near the open end thereof;

said sheet folded into opposing sides having a hinged edge and opposing free edges;

said sheet formable into an open ended polygon when said hinged edge is drawn toward said free edges;

said sheet retained to said tube;

said tube telescopingly collapsed about said polygonal body.

* * * * *